United States Patent
Saxena

(10) Patent No.: US 11,819,582 B2
(45) Date of Patent: Nov. 21, 2023

(54) MODULAR APPARATUS WITH UNIVERSAL BASE FRAME FOR ULTRAVIOLET (UV) LIGHT SANITIZATION OF AN AIRCRAFT AND METHODS FOR PRODUCING SAME

(71) Applicant: HONEYWELL INTERNATIONAL INC., Morris Plains, NJ (US)

(72) Inventor: Sunit Kumar Saxena, Bangalore (IN)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 441 days.

(21) Appl. No.: 17/012,500

(22) Filed: Sep. 4, 2020

(65) Prior Publication Data

US 2022/0023457 A1    Jan. 27, 2022

(30) Foreign Application Priority Data

Jul. 23, 2020 (IN) .............................. 202011031521

(51) Int. Cl.
| | |
|---|---|
| A61L 2/10 | (2006.01) |
| A61L 2/24 | (2006.01) |
| A61L 2/26 | (2006.01) |
| B64F 5/30 | (2017.01) |

(52) U.S. Cl.
CPC ........ *A61L 2/10* (2013.01); *A61L 2/24* (2013.01); *A61L 2/26* (2013.01); *B64F 5/30* (2017.01); *A61L 2202/11* (2013.01); *A61L 2202/14* (2013.01); *A61L 2202/16* (2013.01); *A61L 2202/25* (2013.01)

(58) Field of Classification Search
CPC ..... A61L 2/10; A61L 2202/16; A61L 2202/25
See application file for complete search history.

(56) References Cited

U.S. PATENT DOCUMENTS

| | | | |
|---|---|---|---|
| 8,859,994 B2 | 10/2014 | Deal | |
| 9,280,654 B1 * | 3/2016 | Peterson | ............. H02J 7/00712 |
| 9,500,350 B2 | 11/2016 | McGuire | |
| 10,272,167 B2 | 4/2019 | Starkweather et al. | |
| 10,500,296 B2 | 12/2019 | Kreitenberg | |
| 10,583,213 B2 | 3/2020 | Stibich et al. | |
| 2007/0230197 A1 | 10/2007 | Scannell, Jr. | |

(Continued)

FOREIGN PATENT DOCUMENTS

| | | | |
|---|---|---|---|
| JP | 2018521746 A * | 8/2019 | ............... A61L 2/10 |
| KR | 101118909 B1 | 11/2010 | |
| WO | 2019/143699 A9 | 7/2019 | |

OTHER PUBLICATIONS

JP 2018521746 A_translation.*

*Primary Examiner* — Kevin Joyner
*Assistant Examiner* — Changru Chen
(74) *Attorney, Agent, or Firm* — LORENZ & KOPF, LLP

(57) ABSTRACT

Modular apparatus and methods for ultraviolet (UV) light sanitization of an aircraft. The modular apparatus generally comprises a base frame that is universal, and multiple interchangeable modular kits to adapt the base frame to different aircraft cabin geometries. The base frame has integrated therewith circuitry and devices that control ultraviolet C-spectrum (UVC) light sources that are located on a frame of the modular kit. Various embodiments of the modular kits have five parts, and assemble the same way, for different aircraft cabin geometries.

14 Claims, 7 Drawing Sheets

(56) References Cited

U.S. PATENT DOCUMENTS

| | | | | |
|---|---|---|---|---|
| 2013/0330235 A1* | 12/2013 | Stibich | ..................... | A61L 2/24 |
| | | | | 422/292 |
| 2019/0283545 A1* | 9/2019 | DaSilva | ............... | B60H 3/0035 |
| 2019/0287063 A1* | 9/2019 | Skaaksrud | ........... | G05D 1/0225 |
| 2020/0085983 A1* | 3/2020 | Ramanand | ................ | A61L 2/10 |

* cited by examiner

MODULAR APPARATUS WITH UNIVERSAL BASE FRAME FOR ULTRAVIOLET (UV) LIGHT SANITIZATION OF AN AIRCRAFT AND METHODS FOR PRODUCING SAME

CROSS REFERENCE TO RELATED APPLICATION

This application claims priority to Indian Provisional Patent Application No. 202011031521, filed Jul. 23, 2020, the entire content of which is incorporated by reference herein.

TECHNICAL FIELD

The technical field generally relates to sanitization systems, and more particularly relates to a modular apparatus having a universal base frame for ultraviolet (UV) light sanitization of an aircraft and methods for producing the same.

BACKGROUND

The sanitization of aircraft cabins is important for public health and safety. Recent events have increased demand for efficient and effective sanitization solutions. Some available solutions include using vertically mounted UV C-spectrum (UVC) bulbs on an automated apparatus and using fixed wing trolleys within an aircraft cabin.

However, aircraft cabins come in a variety of geometries and seating configurations. A technical problem is presented in that, to meet sanitization requirements, equipment of different sizes may be needed to reach all target areas and to sanitize different aircraft cabins. In particular, the aircraft cabins of wide body aircraft and narrow body aircraft have different row lengths and numbers of seats per row on each side of an aisle, so equipment used for sanitization must be adaptive if it is to meet both needs.

Therefore, technologically improved methods and apparatus for aircraft sanitization are desirable. Other desirable features and characteristics of the herein described embodiments will become apparent from the subsequent detailed description and the appended claims, taken in conjunction with the accompanying drawings and the foregoing technical field and background.

BRIEF SUMMARY

This summary is provided to describe select concepts in a simplified form that are further described in the Detailed Description. This summary is not intended to identify key or essential features of the claimed subject matter, nor is it intended to be used as an aid in determining the scope of the claimed subject matter.

Provided is a modular apparatus for ultraviolet C-spectrum (UVC) light sanitization of an aircraft. The modular apparatus includes: a base frame that is mobile, incorporating therewith a controller circuit operationally coupled to a user interface configured to receive operator input and provide visual feedback; and a modular kit having a frame with UVC light sources; the base frame having a command outlet configured to attach to the modular kit; the controller circuit configured to: receive from the user interface operator input that includes controlling when the modular apparatus is operating and is not operating; generate, when the modular apparatus is operating, a first number of independent radiation commands, each configured to drive a respective UVC light source; and provide the first number of radiation commands in the command outlet; and the modular kit having a second number of UVC lights, the second number being less than or equal to the first number, the second number of UVC lights being a function of a cabin geometry of the aircraft, the modular kit configured to receive, via the command outlet, individual radiation commands for the second number of UVC lights.

Also provided is a method for employing a modular apparatus for ultraviolet C-spectrum (UVC) light sanitization of an aircraft. The method includes: incorporating a controller circuit operationally coupled to a user interface configured to receive operator input and provide visual feedback on a modular base frame that is mobile; attaching a modular kit with a frame having thereon UV light sources to a command outlet on the base frame; receiving, from the user interface, operator input that includes controlling when the modular apparatus is operating and is not operating; generating by the controller circuit, when the modular apparatus is operating, a first number of independent radiation commands, each configured to drive a respective UVC light source; and providing, by the controller circuit, the first number of radiation commands in the command outlet; and receiving, by the modular kit at the command outlet, a second number of the radiation commands, the second number being less than or equal to the first number, the second number of UVC lights being a function of a cabin geometry of the aircraft; and emitting UVC light, by UV light sources on the modular kit, responsive to the second number of radiation commands.

Furthermore, other desirable features and characteristics of the system and method will become apparent from the subsequent detailed description and the appended claims, taken in conjunction with the accompanying drawings and the preceding background.

BRIEF DESCRIPTION OF THE DRAWINGS

The present application will hereinafter be described in conjunction with the following drawing figures, wherein like numerals denote like elements, and.

DETAILED DESCRIPTION

The following detailed description is merely illustrative in nature and is not intended to limit the embodiments of the subject matter or the application and uses of such embodiments. As used herein, the word "exemplary" means "serving as an example, instance, or illustration." Thus, any embodiment described herein as "exemplary" is not necessarily to be construed as preferred or advantageous over other embodiments. The embodiments described herein are exemplary embodiments provided to enable persons skilled in the art to make or use the invention and not to limit the scope of the invention that is defined by the claims. Furthermore, there is no intention to be bound by any expressed or implied theory presented in the preceding technical field, background, summary, or the following detailed description.

As mentioned, a technical problem is presented in aircraft sanitization in that every aircraft cabin may present a different cabin geometry. Using available equipment for ultra-violet C-spectrum (UVC) light for aircraft sanitization for a variety of cabin geometries can be complex and costly. Accordingly, there is a need for technologically improved solutions that are modular and easily adaptable to different cabin geometries. Exemplary embodiments provide a technologically improved solution taking the form of a universal base frame for ultraviolet (UV) light sanitization of an aircraft and various modular kits that adapt the universal base frame to different aircraft geometries. The base frame is mobile and has integrated therewith circuitry and devices that generate and provide radiation commands for controlling the emission intensity and pattern of a first number of individually controlled of ultra-violet C-spectrum (UVC) light sources. The universal base frame provides these radiation commands via a command outlet that is configured to operably communicate with plurality of interchangeable modular kits. Each modular kit has an easy to assemble aircraft-specific frame (e.g., its size and geometry) and an aircraft-specific number of UVC light sources mounted thereon; in a given aircraft sanitization scenario, the user selects and attaches a modular kit that is aircraft-specific. The modular kit is configured to, when attached, receive the radiation commands via the command outlet and route them to respective UVC light sources. A more detailed description is provided below.

Figure 1:
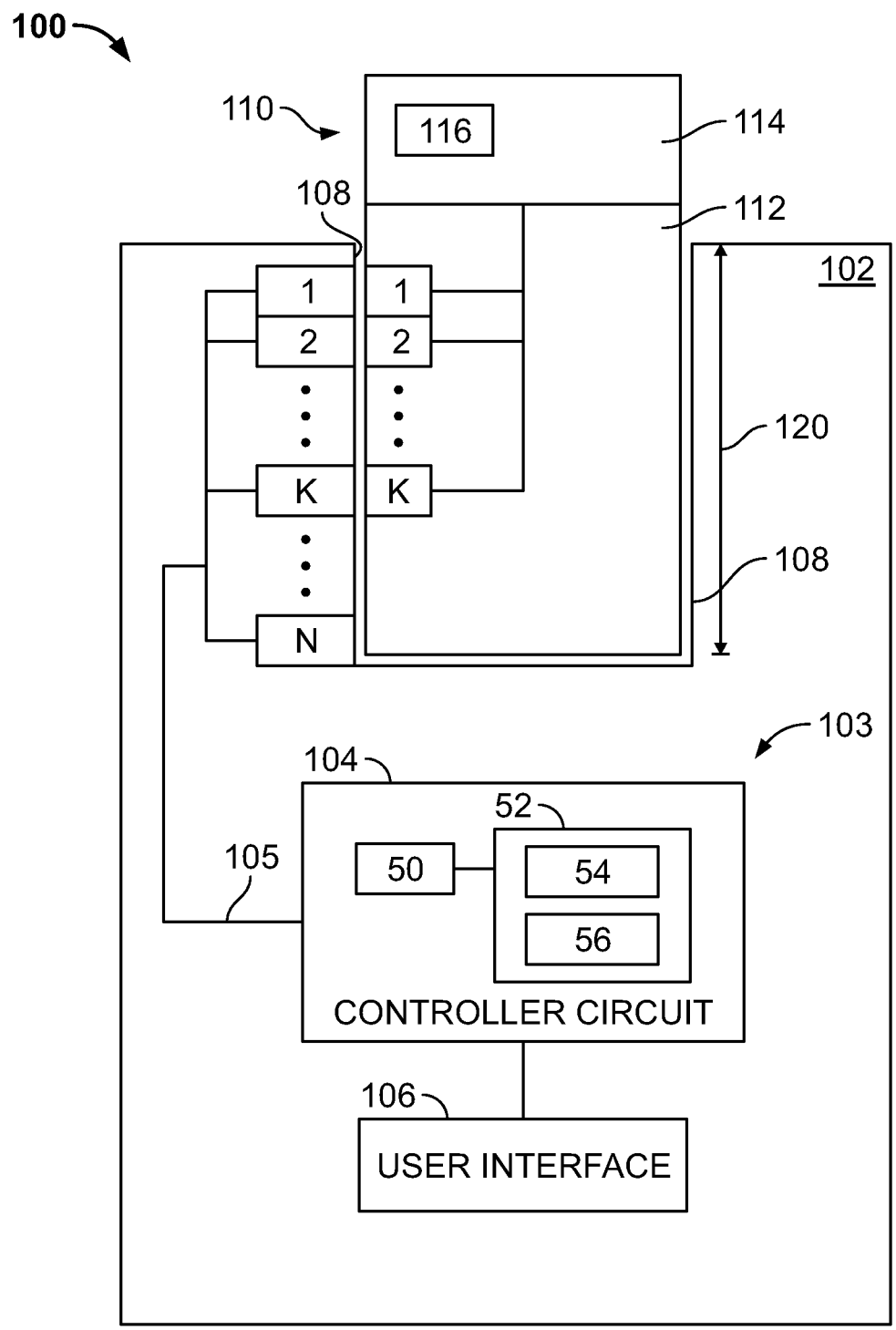
FIGS. 1-2 are illustrations of the functional blocks and structure of a modular apparatus having a universal base frame for ultraviolet (UV) light sanitization of an aircraft, in accordance with an exemplary embodiment.
Figure 2:
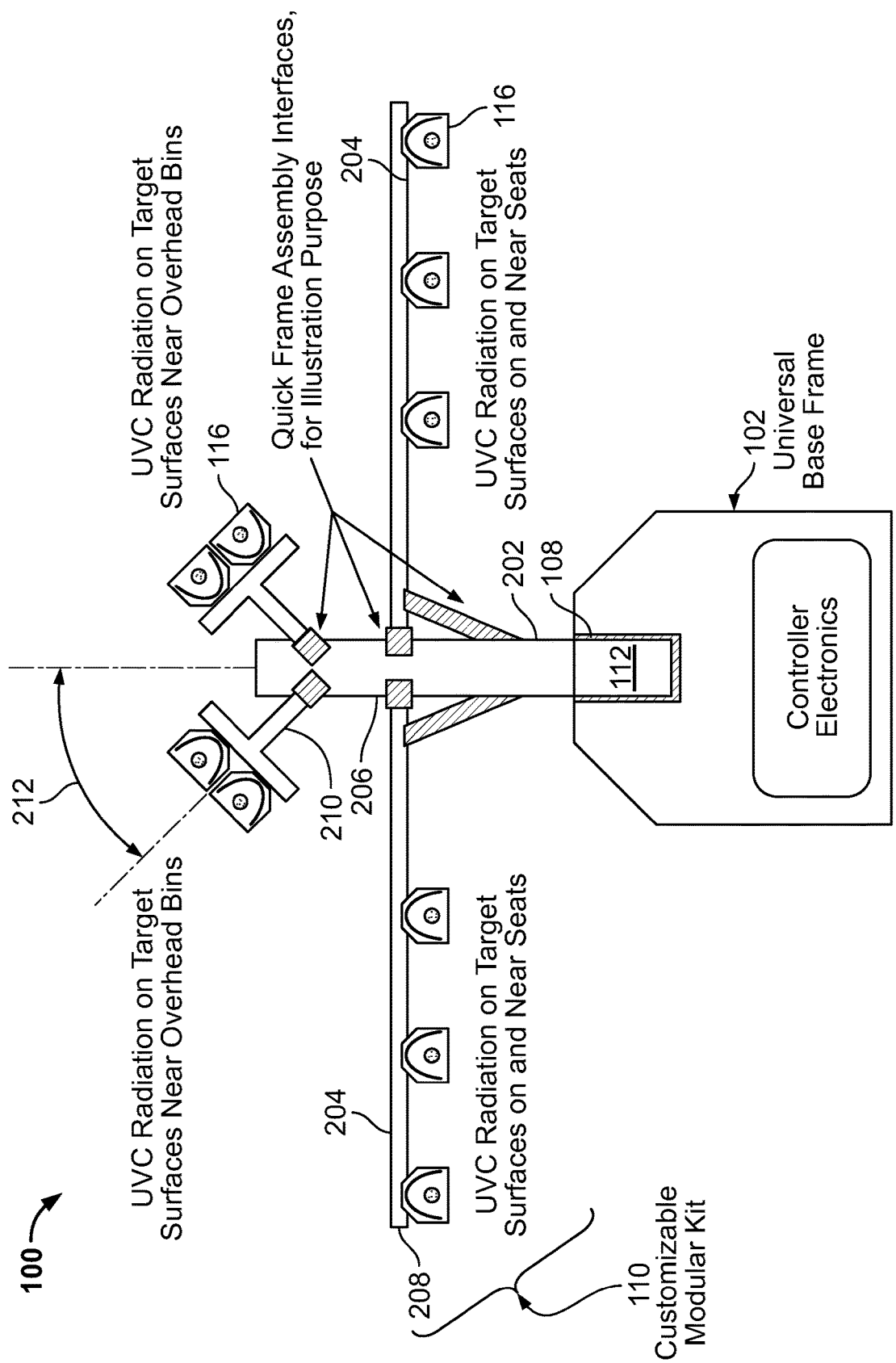

Turning now to FIGS. 1-2, the functional blocks and structure of a modular apparatus 100 are described in more detail. As used herein, the base frame 102 is a mobile frame, such as a rectangular cart or trolley, with wheels for movement. However, in other embodiments, movement of the base frame 102 may be enabled without wheels, and the shape may take various forms. The dimensions of the base frame 102 are limited by aircraft cabin geometry and are specifically sized to universally fit in the aisles of multiple different cabin geometries and different seating configurations. As used herein, cabin geometry references at least a narrow body aircraft and a wide body aircraft. Therefore, the dimensions of the base frame 102 are selected to be slender enough to ensure a universal fit among a plurality of different aircraft, and specifically wide body aircraft and narrow body aircraft.

Controller circuitry 103 is located on the base frame 102. Controller circuitry 103, performs the functions and operations of the modular apparatus 100 and includes at least a user interface 106 and a controller circuit 104. The user interface 106 is configured to receive operator input and provide visual feedback. In various embodiments, the user interface 106 may incorporate one or more user input/output devices, which may be integrated within the base frame 102. In an embodiment, the user interface 106 may be a graphical user interface (GUI) layout for a touchscreen display. In other embodiments, the user interface 106 may include commands and controls for any combination of: a keyboard, an alphanumeric display, and one or more lights that can be illuminated in different colors to provide the alerting described hereinbelow. User input includes controlling when the modular apparatus is operating and when it is not operating. In various embodiments, visual feedback provided by the user interface 106 may be one or more dedicated lightbulbs, as described above, to indicate that the modular apparatus is operating and/or to provide various alerts.

The controller circuit 104 is operationally coupled to the user interface 106. In various embodiments, and as depicted in FIG. 1, the controller circuit 104 may be implemented as an enhanced computer system including a processor 50 configured by programming instructions (for example software program 54 and variables, stored in memory 52). In other embodiments, the controller circuit 104 may take the form of a programmable logic array, application specific circuit, or the like.

The processor 50 may comprise any type of processor or multiple processors, single integrated circuits such as a microprocessor, or any suitable number of integrated circuit devices and/or circuit boards working in cooperation to carry out the described operations, tasks, and functions by manipulating electrical signals representing data bits at memory locations in the system memory, as well as other processing of signals. The memory 52 may comprise RAM memory, ROM memory, flash memory, registers, a hard disk, or another suitable non-transitory short or long-term storage media capable of storing computer-executable programming instructions or other data for execution. The memory 52 may be located on and/or co-located on the same computer chip as the processor 50. Generally, the memory 52 maintains data bits and may be utilized by the processor 50 as storage and/or a scratch pad during operation. Specifically, the memory 52 stores instructions and applications. In some embodiments, a portion of the memory 52 may be a database 56 that is used to store lookup tables or other pre-programmed items such as radiation patterns. Information in the memory 52 may be organized and/or imported from an external data source during an initialization step of a process; it may also be programmed via a user input device.

A novel program 54 includes rules and instructions which, when executed, cause the processor 50 to perform the functions, techniques, and processing tasks associated with the operation of the modular apparatus 100. Novel program 54 and associated stored variables may be stored in a functional form on computer readable media, as depicted, in memory 52. While the depicted exemplary embodiment is described in the context of a fully functioning enhanced computer system, those skilled in the art will recognize that the mechanisms of the present disclosure are capable of being distributed as a program product, with one or more types of non-transitory computer-readable signal bearing media used to store the program and the instructions thereof and carry out the distribution thereof, such as a non-transitory computer readable medium bearing the program 54 and containing computer instructions stored therein for causing a computer processor (such as the processor 50) to perform and execute the program 54. Such a program product may take a variety of forms, and the present disclosure applies equally regardless of the type of computer-readable signal bearing media used to carry out the distribution. Examples of signal bearing media include recordable media such as floppy disks, hard drives, memory cards and optical disks, and transmission media such as digital and analog communication links. It will be appreciated that cloud-based storage and/or other techniques may also be utilized in certain embodiments.

During modular apparatus 100 operation, the processor 50 may load and execute one or more programs, algorithms and rules embodied in the program 54, thereby being programmed with program 54. During execution of program 54, the processor 50 performs the processing activities of the modular apparatus 100, and specifically, generates, when the modular apparatus 100 is operating, a first number (N) of independent radiation commands 105, each configured to drive a respective UVC light source.

In various embodiments, the components of the modular apparatus 100 may be communicatively coupled by any suitable physical or logical means of connecting computer systems and components, including, but not limited to, direct hard-wired connections, fiber optics, infrared and wireless bus technologies.

With continued reference to FIGS. 1-2, a two-dimensional illustration of an embodiment of the modular apparatus 100 is depicted with its bottom near the bottom of the page. The base frame 102 has thereon a command outlet 108 configured to compatibly attach to each of a plurality of modular kits.

The controller circuit 104 is configured to provide the first number (N) of independent radiation commands 105 in the command outlet 108 when the modular apparatus 100 is operating. In FIG. 1, the N different radiation commands 105 are shown to fan out to respective sites with a separate pad, this is one exemplary embodiment. Those with skill in the art will appreciate that, in other embodiments, the N different radiation commands may be provided in one dedicated connection, or on a dedicated bus, using any available multiplexing and demultiplexing communication protocols, as appropriate for assuring the N different radiation commands do not get conflated or mixed up. In various embodiments, each of the N radiation commands turns a respective UVC light source on and off. In various embodiments, each of the N radiation commands additionally alters an UVC emission intensity of a UV light source 116. In various embodiments, each of the N radiation commands additionally causes the UV light source 116 to emit in a continuous or pulsed pattern. The controller circuit 104 may be further configured to reference a predefined radiation pattern to generate the respective radiation command 105 for each of the plurality of UV light sources 116. In various embodiments, the radiation pattern may be one of a plurality of pre-programmed radiation patterns, pre-programmed and stored in memory 52, for example.

The modular kit 110 is shown attached in the command outlet 108. A portion of the modular kit 110 that attaches to the command outlet is referred to as a receiving connector 112. In various embodiments, and as shown in FIG. 2, the geometry of the command outlet 108 is such that it receives the receiving connector 112 therein, providing a fit that is snug and has an overlap 120 with the receiving connector 112 of the modular kit 110 such that it provides structural support for the modular kit 110. The modular kits 110 are interchangeable, based in part on each having a receiving connector 112 that has the same geometric configuration to operably couple to/attach to the command outlet 108. In another aspect, the modular kits 110 are interchangeable based in part on each being configured to receive some or all of the N available radiation commands from the base frame and utilize them for the operation of the UV light sources on the frame. Said differently, where K is a variable, K is the number of radiation commands that a modular kit needs; Each modular kit, such as for narrow body and for wide body, will have a different K number of UCV light sources and will need a respective different K radiation commands.

The modular kit 110 is optimized in several aspects. In a first aspect, the frame 114 of the modular kit 110 is optimized to be easy to assemble and have minimal parts. In exemplary embodiments, the modular kits have five parts that easily assemble.

In a second aspect, the modular kit 110 is optimized for an aircraft-specific cabin geometry. In an embodiment, each modular kit 110 comprises a frame with an extension trunk 202 having the receiving connector 112 on a first end and extend upward therefrom, an extension arm 204 having a proximal end 206 and a distal end 208, the extension arm 204 configured to attach at the proximal end 206 to the extension trunk 202 and extend outward horizontally therefrom. The extension arm 204 having at least one of the second number of UV light sources 116 installed thereon between the distal end 208 and the proximal end 206, and an overhead arm 210 configured to attach to the extension trunk 202 and extend upward at an angle 212 from vertical therefrom, the overhead arm 210 having at least one of the second number of UV light sources 116 installed thereon. In various embodiments, the modular kits 110 have five pieces: one extension trunk, two extension arms, and two overhead arms.

In a third aspect, each modular kit 110 is optimized to have an aircraft-specific number of UV light sources 116 on its frame. Each modular kit comprises a second number (K) of UV light sources 116 that are mechanically coupled to the frame of the modular kit, where K is less than or equal to N. Each UV light source 116 is configured to emit UV-C spectrum light outward from the base frame 102. As mentioned, the emission of the UV-C spectrum light is responsive to a respective radiation command 105. The UV light sources are each a UV-C spectrum (UVC) radiation source, such as a mercury-based lamp or a plurality of LEDs.

Figure 3:
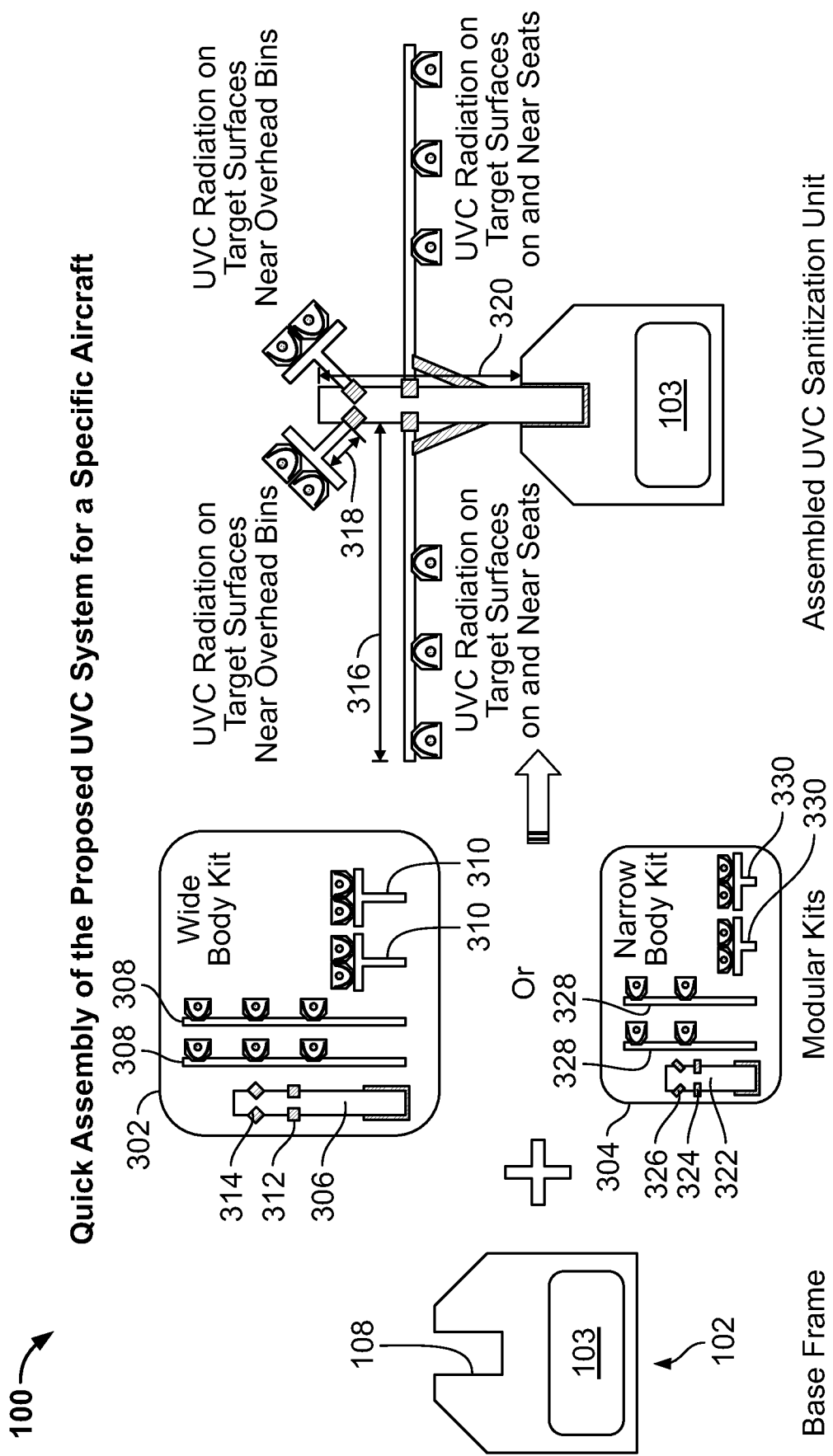
FIGS. 3-4 are illustrations showing a universal base frame for ultraviolet (UV) light sanitization of an aircraft and various modular kits that adapt the universal base frame to different aircraft geometries, in accordance with exemplary embodiments.
Figure 4:
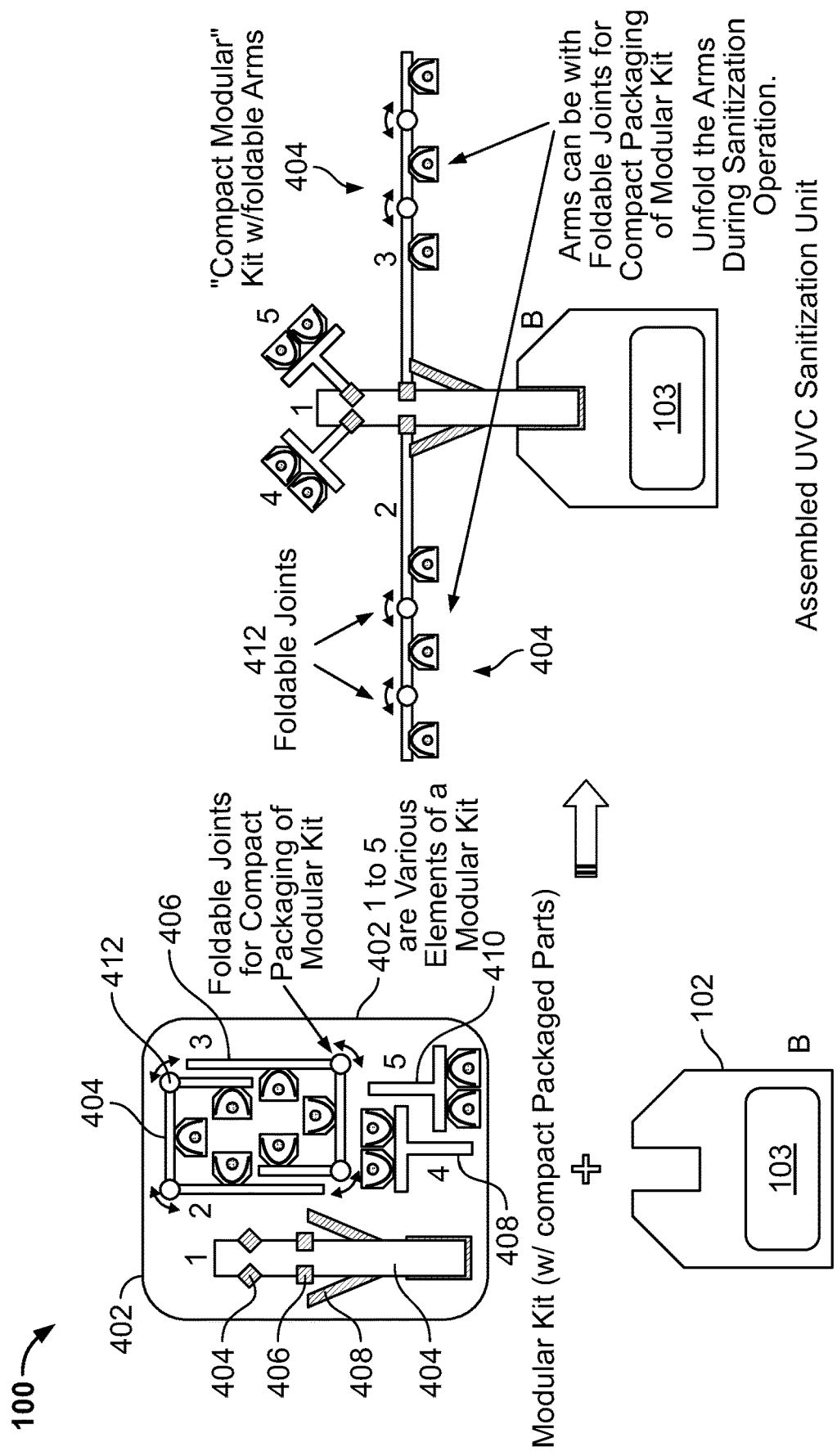

As mentioned, the modular kit 110 is advantageously designed to be easy to assemble and have minimal parts to achieve its sanitization objective for various aircraft cabin geometries. Turning now to FIGS. 3-4, various embodiments of the modular kit 110, suitable for different aircraft cabin geometries, are described in connection with the base frame 102. In FIG. 3, a wide body modular kit 302 is shown, having five pieces: the extension trunk 306, two extension arms 308, and two overhead arms 310. In the example, the extension arms 308 each have three UV light sources 116. Two receiving sockets 312 on the extension trunk 306 are configured to receive the extension arms 308. Two receiving sockets 314 on the extension trunk 306 are configured to receive the overhead arms 310. Assembling the modular kit 302 includes placing the extension arms 308 in the receiving sockets 312 and placing the overhead arms 310 in the receiving sockets 314.

A narrow body modular kit 304, also having 5 pieces, is also shown. The five pieces include: the extension trunk 322, two extension arms 328, and two overhead arms 330. In the example, the extension arms 328 each have two UV light sources 116. Two receiving sockets 324 on the extension trunk 322 are configured to receive the extension arms 328. Two receiving sockets 326 on the extension trunk 322 are configured to receive the overhead arms 330. Assembling the modular kit 304 includes placing the extension arms 328 in the receiving sockets 324 and placing the overhead arms 330 in the receiving sockets 326.

As one may appreciate, and as shown with relative sizes in FIG. 3, a trunk length 320 for a wide body modular kit 302 may be larger than a trunk length 320 for a narrow body modular kit 304; an arm length 316 for a wide body modular kit 302 may be larger than an arm length 316 for a narrow body modular kit 304; and an overhead length 318 for a wide body modular kit 302 may be larger than an overhead length 318 for a narrow body modular kit 304. Said differently, the trunk length 320, arm length 316, and overhead length 318 may each be a function of the cabin geometry of the aircraft.

In yet another embodiment, as shown in FIG. 4, the extension arms 404 and 406 may have one or more joints 412 that enable at least a partial folding of the respective extension arm, for an even more compact modular kit 402.

Figure 5:
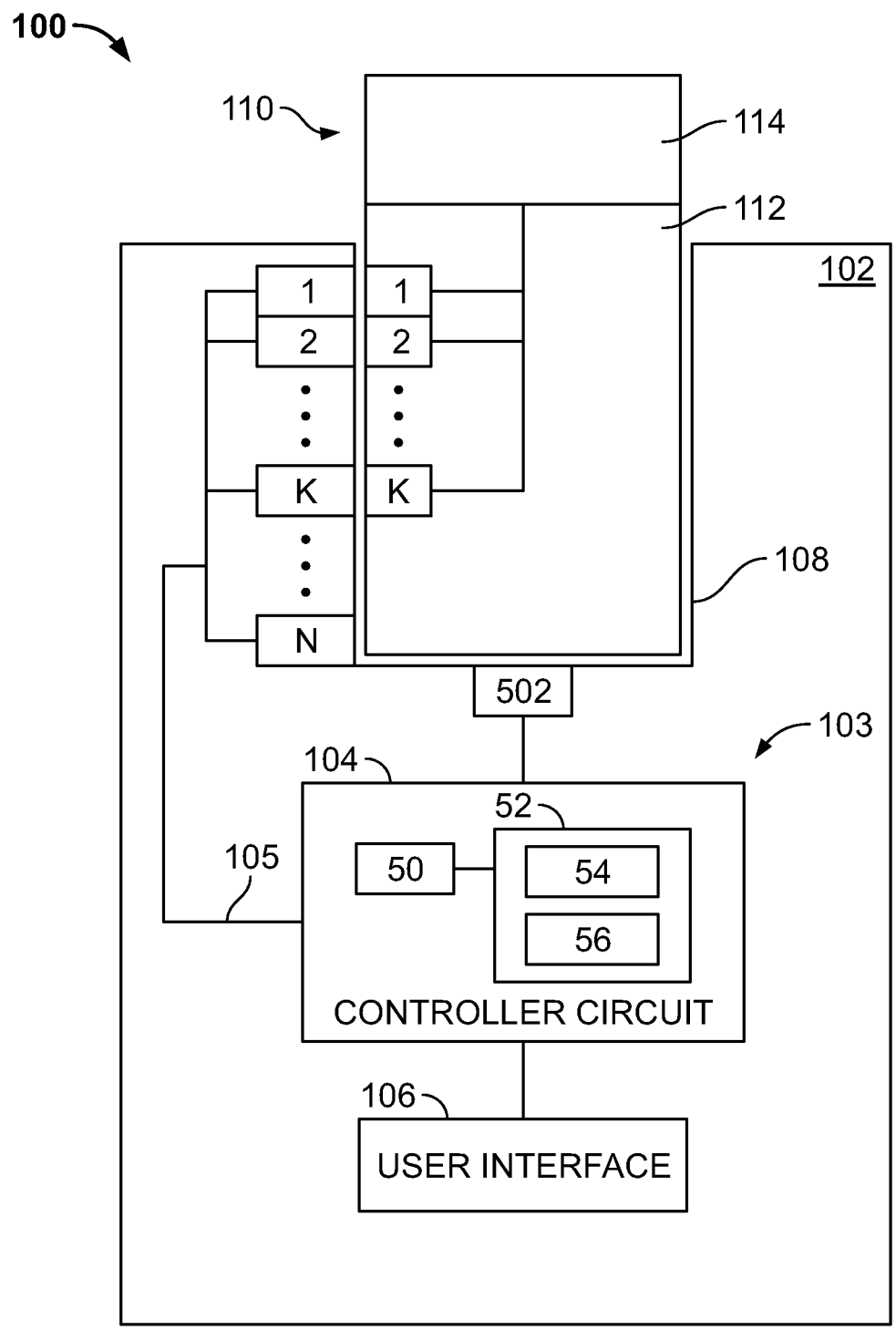
FIGS. 5-6 are illustrations of variations of a modular apparatus having a universal base frame for ultraviolet (UV) light sanitization of an aircraft, in accordance with exemplary embodiments.

In various embodiments, as shown in FIG. 5, the base frame 102 may have one or more sensors located within the command outlet 108. For example, a presence sensor 502 may be oriented and configured to detect a secured communication between the command outlet 108 and the modular kit 110. The controller circuit 104 may be configured to process input from the presence sensor 502 to determine when the modular kit 110 has been attached to the command outlet 108 in the base frame 102, and to generate an alert when an insufficient connection is detected. In another embodiment, the sensor 502 may be used to detect what kind of modular kit 110 is attached to the base frame 102. Using this input, the controller circuit may additionally be configured to reference an aircraft-specific UV specification for the aircraft to determine whether the attached modular kit 110 is incorrectly selected (e.g., incorrect body size: detecting a body size of the modular kit attached, referencing a specification for this aircraft and determining that this is a wide body plane, but a narrow body modular kit has been attached, or that the wrong seating configuration is supported by the attached modular kit), and generate visual feedback indicating a body size error when the modular kit is incorrectly selected. In another embodiment, the sensor 502 may detect a manufacturing source of the modular kit, determine whether the manufacturing source is supported, and generate visual feedback indicating an unsupported modular kit when the modular kit is not supported.

Figure 6:
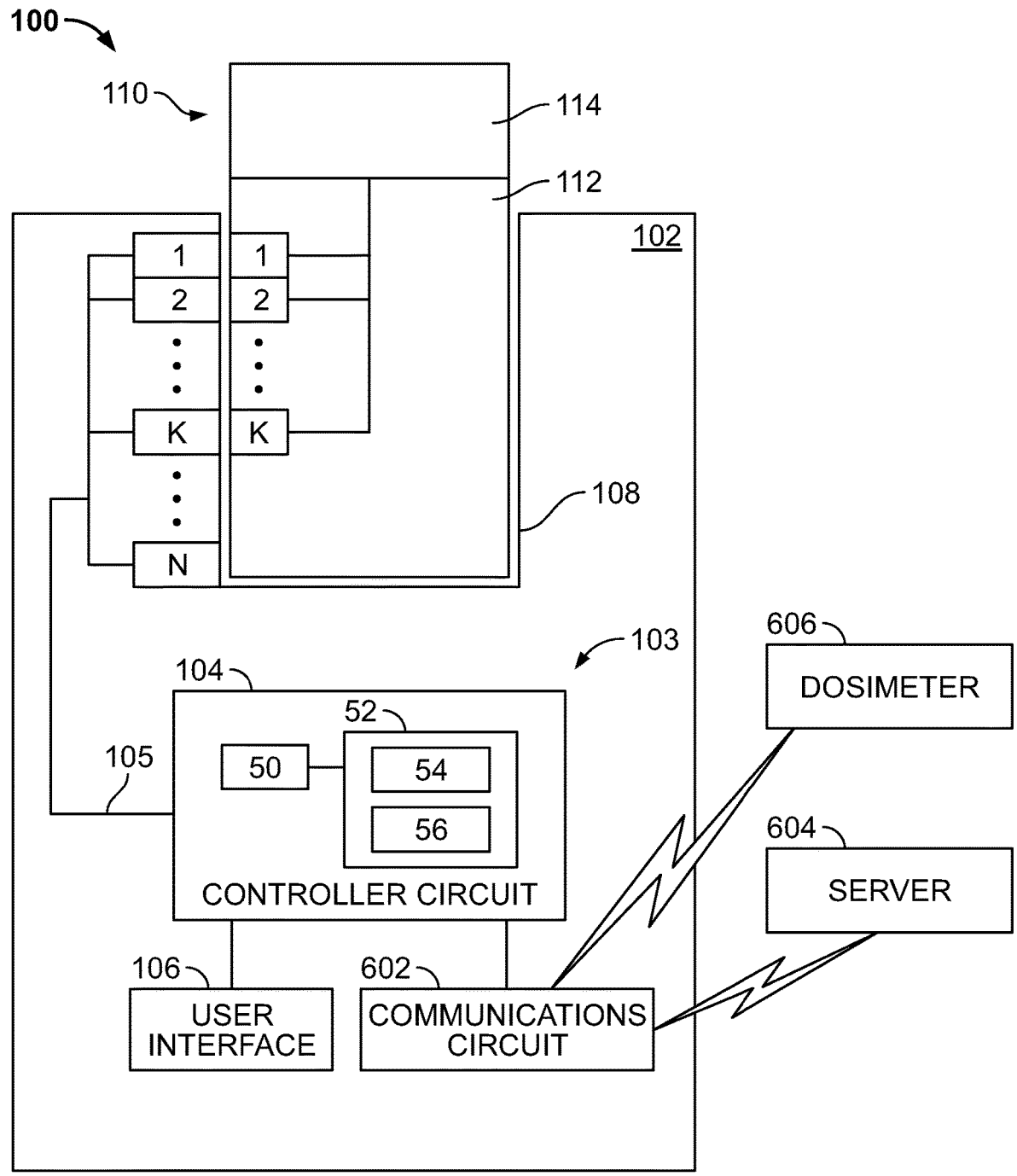

Turning now to FIG. 6, in various embodiments, the controller circuitry 103 further includes a communications circuit 602 located on the base frame 102 and operationally coupled to the controller circuit 104. The communications circuit 602 is configured to support instantaneous (i.e., real time or current) communications between the base frame 102 and the one or more external data source(s). The communications circuit 602 may include one or more network interfaces and can be implemented using any suitable method and apparatus. In various embodiments, the communications circuit 602 may support communication with technicians, and/or one or more storage interfaces for direct connection to memory 52. As a functional block, the communications circuit 602 represents one or more transmitters, receivers, and the supporting communications hardware and software required for the modular apparatus 100 to communicate with the various external data source(s), such as server 604 and/or a dosimeter 606.

In an example embodiment, the modular apparatus 100 may utilize the communications circuit 602 to communicate with one or more dosimeters 606, distributed throughout the cabin of the aircraft. For example. The controller circuit 104 may receive UV dosing information from at least one dosimeter 606 located external to the modular apparatus; and generate or modify the first number of radiation commands based on the received UV dosing information.

Figure 7:
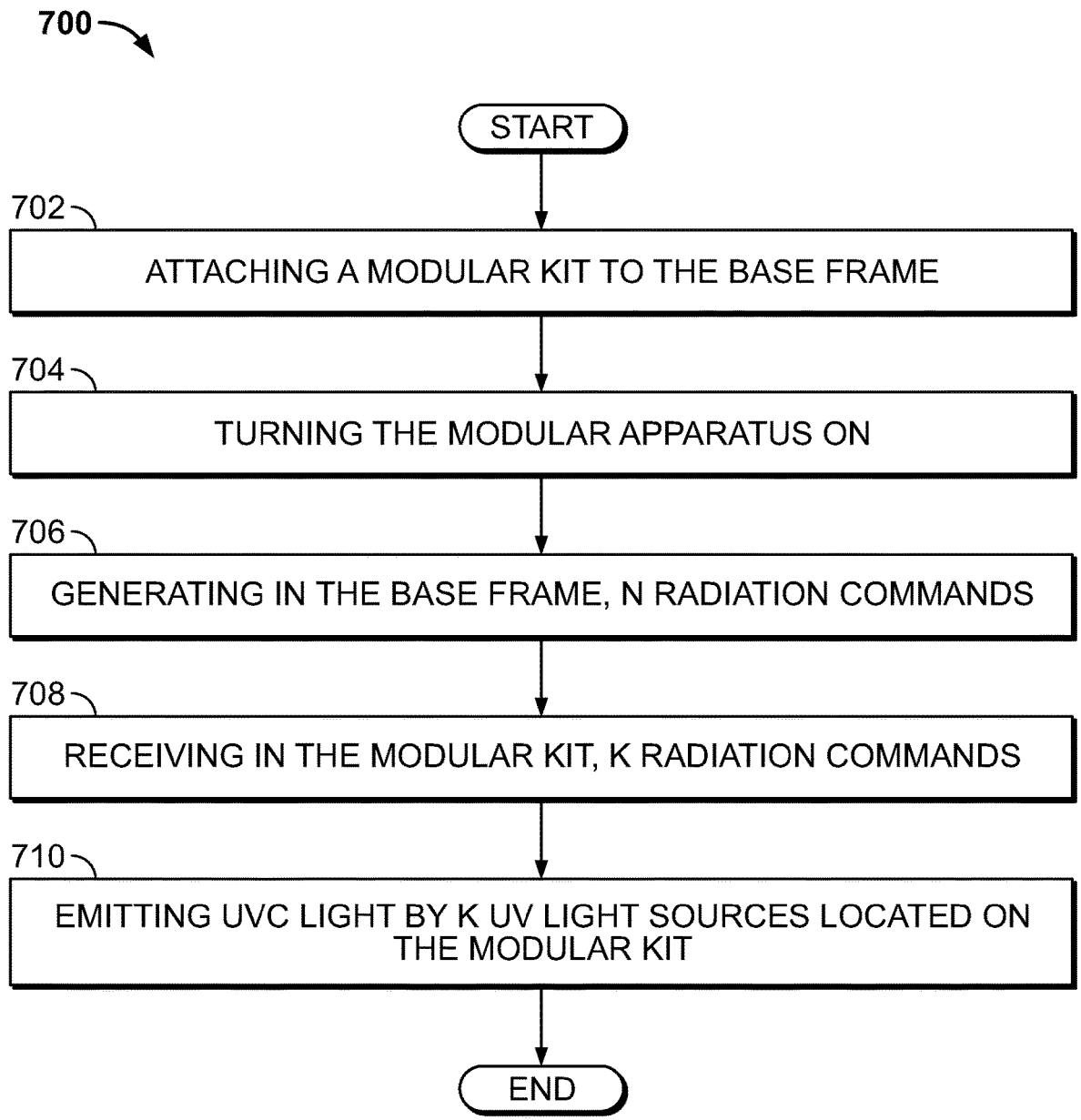
FIG. 7 is a flow chart for a method associated with a modular apparatus having a universal base frame for ultraviolet (UV) light sanitization of an aircraft, in accordance with herein described embodiments.

Referring now to FIG. 7 and with continued reference to FIGS. 1-6, a flow chart is provided for a method 700 for the modular apparatus 100, in accordance with various exemplary embodiments. For illustrative purposes, the following description of method 700 may refer to elements mentioned above in connection with FIGS. 1-6. In practice, portions of method 700 may be performed by different components of the described system. It should be appreciated that method 700 may include any number of additional or alternative tasks, the tasks shown in FIG. 7 need not be performed in the illustrated order, and method 700 may be incorporated into a more comprehensive procedure or method having additional functionality not described in detail herein. Moreover, one or more of the tasks shown in FIG. 7 could be omitted from an embodiment of the method 700 if the intended overall functionality remains intact.

Before operation, the controller circuit 104 is initialized. As mentioned above, initialization may comprise uploading or updating instructions and applications, program 54, and the like. Initialization at may also include identifying dosimeters 606 and/or external servers 604, and the communication protocols to use with each of them.

At 702, a modular kit 110 is attached to the base frame 102. The description of the modular kits and how they attach are described in detail above. In embodiments that use sensors to detect the presence of the modular kit 110, its aircraft cabin type, and/or its manufacturer, these operations may occur at 702. At 704, the modular apparatus 100 is turned on.

At 706, the controller circuit 104 in the base frame 102 generates the N radiation commands 105 for controlling UVC emissions from N UV light sources. In some embodiments, at 706, the controller circuit 104 receives UV dosing information from at least one dosimeter 606 located external to the modular apparatus, and within the aircraft cabin; and, generates the radiation commands 105 based on the received UV dosing information. The dosimeter 122 may be located on a seat, in an overhead compartment area, in a bathroom, or the like. Dosimeters 606 may be affixed or portable.

At 708, the modular kit receives K radiation commands, one each for its K UV light sources 116 installed thereon. At 710, each of the K UV light sources 116 on the modular kit emits UVC light responsive to the respective radiation command.

Thus, a technologically improved solution for aircraft sanitization in the form of a modular apparatus for ultraviolet (UV) light sanitization of an aircraft has been presented. As is readily appreciated, the above examples of the apparatus 100 are non-limiting.

Those of skill in the art will appreciate that the various illustrative logical blocks, modules, circuits, and algorithm steps described in connection with the embodiments disclosed herein may be implemented as electronic hardware, computer software, or combinations of both. Some of the embodiments and implementations are described above in terms of functional and/or logical block components (or modules) and various processing steps. However, it should be appreciated that such block components (or modules) may be realized by any number of hardware, software, and/or firmware components configured to perform the specified functions. To clearly illustrate the interchangeability of hardware and software, various illustrative components, blocks, modules, circuits, and steps have been described above generally in terms of their functionality. Whether such functionality is implemented as hardware or software depends upon the application and design constraints imposed on the overall system.

Skilled artisans may implement the described functionality in varying ways for each application, but such implementation decisions should not be interpreted as causing a departure from the scope of the present invention. For example, an embodiment of a system or a component may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that embodiments described herein are merely exemplary implementations.

Further, the various illustrative logical blocks, modules, and circuits described in connection with the embodiments disclosed herein may be implemented or performed with a general-purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of the method or algorithm described in connection with the embodiments disclosed herein may be embodied directly in hardware, in a software module executed by a controller or processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC.

In this document, relational terms such as first and second, and the like may be used solely to distinguish one entity or action from another entity or action without necessarily requiring or implying any actual such relationship or order between such entities or actions. Numerical ordinals such as "first," "second," "third," etc. simply denote different singles of a plurality and do not imply any order or sequence unless specifically defined by the claim language. The sequence of the text in any of the claims does not imply that process steps must be performed in a temporal or logical order according to such sequence unless it is specifically defined by the language of the claim. When "or" is used herein, it is the logical or mathematical or, also called the "inclusive or." Accordingly, A or B is true for the three cases: A is true, B is true, and, A and B are true. In some cases, the exclusive "or" is constructed with "and;" for example, "one from the set including A and B" is true for the two cases: A is true, and B is true.

Furthermore, depending on the context, words such as "connect" or "coupled to" used in describing a relationship between different elements do not imply that a direct physical connection must be made between these elements. For example, two elements may be connected to each other physically, electronically, logically, or in any other manner, through one or more additional elements.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A modular apparatus for ultraviolet C-spectrum (UVC) light sanitization of an aircraft, comprising:
    a base frame that is mobile, incorporating therewith a controller circuit operationally coupled to a user interface configured to receive operator input and provide visual feedback; and
    a modular kit having a frame with UVC light sources;
    the base frame having a command outlet configured to attach to the modular kit;
    the controller circuit configured to:
        receive from the user interface operator input that includes controlling when the modular apparatus is operating and is not operating;
        generate, when the modular apparatus is operating, a first number of independent radiation commands, each configured to drive a respective UVC light source; and
        provide the first number of radiation commands in the command outlet; and
    the modular kit having a second number of UVC lights, the second number being less than or equal to the first number, the second number of UVC lights being a function of a cabin geometry of the aircraft, the modular kit configured to receive, via the command outlet, individual radiation commands for the second number of UVC lights,
    wherein the controller circuit is further configured to:
        detect a body size of the modular kit;
        reference an aircraft-specific UV specification for the aircraft to determine whether the modular kit is incorrectly selected; and
        generate visual feedback indicating a body size error when the modular kit is incorrectly selected.

2. The modular apparatus of claim 1, wherein the base frame further comprises a presence sensor oriented and configured to detect a secured communication between the command outlet and the modular kit; and
    the controller circuit is configured to process input from the presence sensor to determine when the modular kit has been attached to the command outlet in the base frame.

3. The modular apparatus of claim 2, wherein the base frame has a presence sensor oriented and configured to detect a secured communication between the command outlet and the modular kit; and wherein the controller circuit is configured to process input from the presence sensor to determine when there is an insufficient connection between the modular kit and the command outlet in the base frame.

4. The modular apparatus of claim 1, wherein the controller circuit is further configured to:
    detect a manufacturing source of the modular kit;
    determine whether the manufacturing source is supported; and
    generate visual feedback indicating an unsupported modular kit when the modular kit is not supported.

5. The modular apparatus of claim 1, wherein the frame of the modular kit comprises:

an extension trunk having a receiving connector configured to attach to the command outlet on a first end and extend upward therefrom;

an extension arm having a proximal end and a distal end, the extension arm configured to attach at the proximal end to the extension trunk and extend outward therefrom, the extension arm having at least one of the second number of UV light sources installed thereon between the distal end and the proximal end; and an overhead arm configured to attach to the extension trunk and extend upward therefrom, the overhead arm having at least one of the second number of UV light sources installed thereon.

6. The modular apparatus of claim 5, wherein:
the extension trunk has a trunk length;
the extension arm has an arm length; and
the overhead arm has an overhead length; and
the trunk length, the arm length, and the overhead length are each a function of the cabin geometry of the aircraft.

7. The modular apparatus of claim 6, wherein:
the extension arm is one of a first plurality extension arms; and
the overhead arm is one of a second plurality overhead arms.

8. The modular apparatus of claim 5, wherein:
the at least one of the second number of UV light sources between the distal end and the proximal end of the extension arm has an emission intensity that is a function of the cabin geometry of the aircraft, responsive to the radiation commands; and the at least one of the second number of UV light sources installed on the overhead arm has an emission intensity that is a function of the cabin geometry of the aircraft, responsive to the radiation commands.

9. The modular apparatus of claim 1, wherein the controller circuit is further configured to reference a predefined radiation pattern to generate the radiation commands.

10. The modular apparatus of claim 9, wherein the radiation pattern is one of a plurality of pre-programmed radiation patterns, and wherein the plurality of radiation patterns includes a high, a medium, and a low intensity UV C-spectrum light.

11. The modular apparatus of claim 10, wherein the radiation pattern further includes pulsing or continuous radiation.

12. The modular apparatus of claim 1, further comprising a communication circuit on the base frame, operationally coupled to the controller circuit and configured to communicate with a dosimeter located external to the modular apparatus.

13. The modular apparatus of claim 12, wherein the controller circuit is further configured to:
receive UV dosing information from the dosimeter located external to the modular apparatus; and
generate the first number of radiation commands based on the received UV dosing information.

14. The modular apparatus of claim 7, wherein at least one of the extension arms has at least one joint enabling it to fold.

* * * * *